(12) United States Patent
Tsujimoto et al.

(10) Patent No.: US 9,034,130 B2
(45) Date of Patent: May 19, 2015

(54) METHOD AND APPARATUS FOR ARRANGING GRANULAR MATERIAL

(75) Inventors: Yoshio Tsujimoto, Osaka (JP); Masaki Nakakado, Osaka (JP)

(73) Assignee: ZUIKO CORPORATION, Osaka (JP)

( * ) Notice: Subject to any disclaimer, the term of this patent is extended or adjusted under 35 U.S.C. 154(b) by 98 days.

(21) Appl. No.: 13/977,132

(22) PCT Filed: Feb. 2, 2012

(86) PCT No.: PCT/JP2012/052372
§ 371 (c)(1),
(2), (4) Date: Jun. 28, 2013

(87) PCT Pub. No.: WO2012/108331
PCT Pub. Date: Aug. 16, 2012

(65) Prior Publication Data
US 2013/0284361 A1      Oct. 31, 2013

(30) Foreign Application Priority Data
Feb. 10, 2011    (JP) .................... 2011-027131

(51) Int. Cl.
| | |
|---|---|
| *A61F 13/532* | (2006.01) |
| *B32B 5/30* | (2006.01) |
| *B32B 37/24* | (2006.01) |
| *B32B 5/16* | (2006.01) |

(Continued)

(52) U.S. Cl.
CPC .............. *B32B 5/16* (2013.01); *A61F 13/15658* (2013.01); *A61F 2013/530562* (2013.01); *B32B 5/30* (2013.01); *B32B 37/24* (2013.01); *A61F 13/15617* (2013.01); *A61F 13/5323* (2013.01)

(58) Field of Classification Search
CPC ........... A61F 13/15658; A61F 13/5323; A61F 2013/530562; B32B 5/16; B32B 5/30; B32B 37/24; B05C 19/00; B05C 19/008
USPC .............................. 156/73.1, 276, 285, 308.4
See application file for complete search history.

(56) References Cited

U.S. PATENT DOCUMENTS

| | | | |
|---|---|---|---|
| 7,524,449 B2 * | 4/2009 | Walsh et al. .................. | 264/511 |
| 2002/0095127 A1 * | 7/2002 | Fish et al. ..................... | 604/368 |

(Continued)

FOREIGN PATENT DOCUMENTS

| | | | |
|---|---|---|---|
| JP | 2004-000830 A | 1/2004 | |
| JP | 2007-130818 A | 5/2007 | |

(Continued)

OTHER PUBLICATIONS

International Search Report for corresponding International Application No. PCT/JP2012/052372 mailed May 1, 2012.

*Primary Examiner* — Michael Tolin
(74) *Attorney, Agent, or Firm* — Renner, Otto, Boisselle & Sklar, LLP

(57) ABSTRACT

A method includes steps of carrying an air-permeable web while holding the first surface of the web on a carrying surface; dispensing powder particles onto the second surface of the web; and while drawing the first air from a plurality of suction holes in the carrying surface through the web, thereby holding the powder particles in a predetermined pattern on the second surface of the web, discharging the second air toward the web through a discharge hole open in a non-suction area, whereby the powder particles on non-suction areas are blown away by the second air, thus arranging the powder particles in a predetermined pattern on the web.

9 Claims, 11 Drawing Sheets

(51) Int. Cl.
*A61F 13/15* (2006.01)
*A61F 13/53* (2006.01)

(56) References Cited

U.S. PATENT DOCUMENTS

2006/0021695 A1 2/2006 Blessing et al.
2007/0246147 A1* 10/2007 Venturino et al. ............ 156/73.1
2010/0114049 A1 5/2010 Noda et al.

FOREIGN PATENT DOCUMENTS

| JP | 2008-507384 A | 3/2008 |
| JP | 2008-237381 A | 10/2008 |
| WO | WO 2006/015138 A1 | 2/2006 |

* cited by examiner

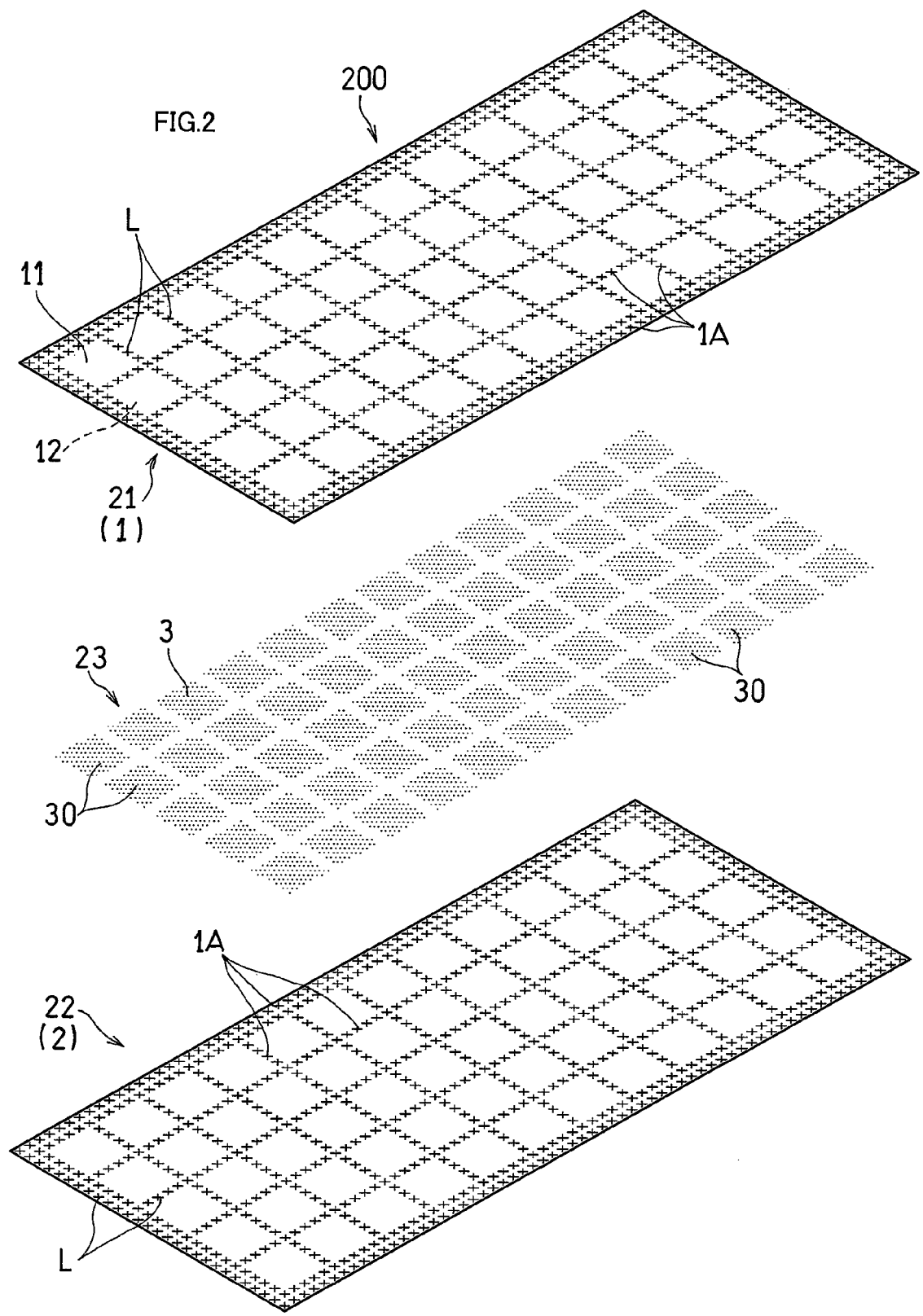

METHOD AND APPARATUS FOR ARRANGING GRANULAR MATERIAL

TECHNICAL FIELD

The present invention relates to a technique for arranging aggregate groups of granular particles on an air-permeable carrier web in a predetermined pattern.

BACKGROUND ART

Disposable worn articles, such as disposable diapers or pants or feminine sanitary supplies, have an absorbent body thereon for absorbing body fluid. Such an absorbent body has a sandwich structure including an absorbent core between two webs.

It has recently been proposed to use only a powdery absorbent polymer as an absorbent core, without using a fluff pulp (First Patent Document). In this case, a large number of aggregate groups of granular particles are arranged while being separated from one another lengthwise and crosswise, and two webs are sealed (attached) together along the gaps between the aggregate groups, thereby holding the arrangement pattern of the aggregate groups.

CITATION LIST

Patent Literature

First Patent Document: WO2006/015138 (front page)

SUMMARY OF INVENTION

Technical Problem

However, if granular particles remain in areas where the carrier web and the cover web are sealed together with granular particles arranged therebetween in a predetermined pattern, the attachment between the webs interposing granular particles therebetween can more easily come off.

In such a case, when attaching the webs together, granular particles may get caught in the sealer device, resulting in a seal failure.

It is therefore an object of the present invention to provide a method and an apparatus for arranging granular particles, whereby aggregate groups of granular particles can be arranged in a predetermined pattern while preventing some granular particles from moving out of predetermined areas.

Solution to Problem

In order to achieve the object set forth above, a method of the present invention is a method for arranging a plurality of granular particles in each of a plurality of arrangement areas which are partitioned from one another in a predetermined pattern, the method including the steps of carrying an air-permeable carrier web along a predetermined carrying path while holding a first surface of the carrier web on a carrying surface of a carrier device; dispensing the granular particles onto a second surface, opposite to the first surface, of the carrier web being carried; drawing a first air from a plurality of suction holes formed in the carrying surface through the carrier web, thereby holding some of the plurality of granular particles on each suction area on the second surface of the carrier web corresponding to one of the suction holes; and while drawing the first air, discharging a second air from a second air discharge hole open in a non-suction area corresponding to the carrying surface between one of the plurality of suction holes and another toward the second surface of the carrier web, whereby some other ones of the plurality of granular particles on the non-suction area are blown away by the second air having passed through the carrier web via the second surface toward at least one of the suction areas, thus arranging the granular particles in each of the arrangement areas in the predetermined pattern on the carrier web.

On the other hand, the present apparatus includes: a carrier device for carrying an air-permeable carrier web along a predetermined carrying path while holding a first surface of the carrier web on a carrying surface thereof; a dispenser device for dispensing the granular particles onto a second surface, opposite to the first surface, of the carrier web being carried; a sucker (drawing) device including a plurality of suction holes formed in the carrying surface for drawing a first air into the suction holes through the carrier web, thereby sucking some of the plurality of granular particles onto each suction area on the second surface of the carrier web corresponding to one of the suction holes; and a discharger device including a second air discharge hole open in a non-suction area corresponding to the carrying surface between one of the plurality of suction holes and another for discharging the second air from the discharge hole toward the second surface of the carrier web, while the first air is being drawn, whereby some other ones of the plurality of granular particles on the non-suction area are blown away by the second air having passed through the carrier web via the second surface.

Advantageous Effects of Invention

The first air is drawn into the plurality of suction holes formed in the carrying surface through the carrier web, thereby holding granular particles on the carrier web in accordance with the pattern, while the second air passes through the carrier web to blow away granular particles in the non-suction area of the carrier web. The blown granular particles are drawn onto suction areas on the carrier web corresponding to the suction holes, thus arranging the granular particles in a predetermined pattern on the carrier web.

BRIEF DESCRIPTION OF DRAWINGS

FIG. 2 is an exploded perspective view of an absorbent body of the worn article.

DESCRIPTION OF EMBODIMENTS

Figure 1:
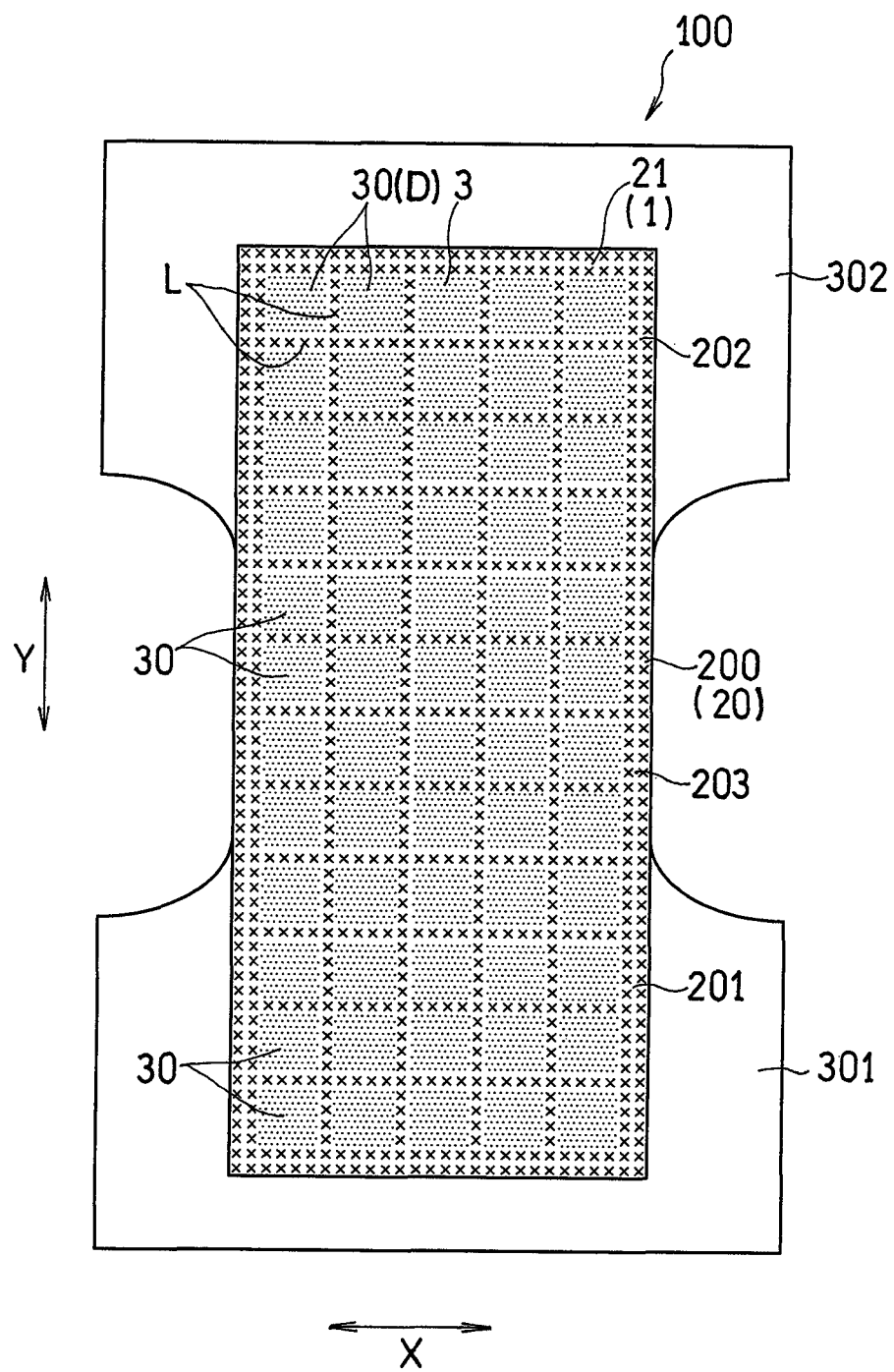
FIG. 1 is a plan view of a worn article according to Embodiment 1 of the present invention.

In a preferred embodiment of the present method, the method further includes the steps of: after the step of arranging the granular particles in the predetermined pattern, covering the second surface of the carrier web and the granular particles by a cover web, thereby producing a sandwich structure; and attaching the carrier web and the cover web together over a portion corresponding to the non-suction area in order to prevent the granular particles in the arrangement areas arranged in the predetermined pattern from moving from one of the plurality of arrangement areas to another.

On the other hand, in a preferred embodiment of the present apparatus, the apparatus further includes: a guide device for guiding the cover web onto the carrying path, while the suction and the discharge are being performed, in order to produce a sandwich structure in which the second surface of the carrier web and the granular particles are covered by a cover web; and an attachment device for attaching the carrier web and the cover web together over a portion corresponding to the non-suction area in order to prevent the granular particles in the arrangement areas arranged in the predetermined pattern from moving from one of the plurality of arrangement areas to another.

In these cases, some of the granular particles arranged in the predetermined pattern are unlikely to move out onto the non-suction area, and will not be interposed between the carrier web and the cover web in the non-suction area. Thus, a failure is unlikely to occur in the seal between the webs, and it is possible to prevent the webs from peeling off of each other in the sealed portions.

While the attachment in the present method may be done by using an adhesive, as well as welding, in a more preferred embodiment of the present method, the attachment step is performed by welding the webs together.

While the attachment in the present apparatus may be done by using an adhesive, as well as welding, in a more preferred embodiment of the present apparatus, the attachment device is a welder device for welding the webs together.

Where the webs are attached together using an adhesive, the webs can be attached together even if a slight amount of granular particles is left in the non-suction area between the webs; however, where the webs are welded together, granular particles, which is a foreign matter, being left in the non-suction area will significantly lower the reliability of the attachment.

Therefore, where the webs are attached together by welding, advantageous effects of the present method will be more pronounced.

In a more preferred embodiment of the present method, the method further includes the step of giving at least a part of the first air a flow component flowing in a direction along the second surface of the carrier web by means of an airflow deflector opposing the second surface of the carrier web, thereby moving the granular particles on the non-suction area on the carrier web toward the suction areas, thus arranging the granular particles in the predetermined pattern on the carrier web.

On the other hand, in a more preferred embodiment of the present apparatus, the apparatus further includes an airflow deflector opposing the second surface of the carrier web, upstream of the guide device along the carrying path of the carrier web, for giving at least a part of the first air a flow component flowing in a direction along the second surface of the carrier web.

In these cases, the airflow deflector, opposing the second surface of the carrier web, inhibits the flow of the first air in the normal direction perpendicular to the second surface. Therefore, a part of the first air is given a flow component flowing in the direction along the second surface. The flow component causes the granular particles in the non-suction area on the carrier web to move toward the suction areas along the second surface of the carrier web. Thus, a plurality of granular particles are arranged in each of the arrangement areas in the predetermined pattern, and it is possible to prevent granular particles from moving out of the suction areas in the predetermined pattern.

EMBODIMENTS

The present invention will be understood more clearly from the following description of preferred embodiments taken in conjunction with the accompanying drawings. Note however that the embodiments and the drawings are merely illustrative and should not be taken to define the scope of the present invention. The scope of the present invention shall be defined only by the appended claims. In the accompanying drawings, like reference numerals denote like components throughout the plurality of figures.

Embodiment 1

Embodiment 1 of the present invention will now be described with reference to the drawings.

FIGS. 1 to 7 show Embodiment 1.

Worn Article 100:

As shown in FIG. 1, a worn article 100 of the present embodiment includes an absorbent body (diaper body) 200, a front girth portion 301, and a back girth portion 302. The absorbent body 200 includes a front portion 201 covering the front torso of the wearer, a back portion 202 covering the back torso of the wearer, and a crotch portion 203 covering the crotch between the front portion 201 and the back portion 202.

The crotch portion 203 is continuous with the front portion 201 and the back portion 202, and extends in the longitudinal direction perpendicular to the girth direction. The front girth portion 301 and the back girth portion 302 may be attached together when worn, or may be attached together in advance before being worn.

The absorbent body 200 may be provided with three-dimensional gathers (not shown).

The absorbent body 200 may be formed with around-the-leg portions narrowed along the legs of the wearer.

Moreover, an elastic member for fitting the worn article 100 to the wearer may be provided in portions of the absorbent body 200 which are to be present around the legs. The elastic member may be, for example, a plurality of rubber threads or rubber tapes, a film, or a material including a thermoplastic resin, or the like. These materials may be provided on the front portion 201 and the back portion 202 as elastic members for fitting the worn article 100 to the wearer.

Figure 3A:
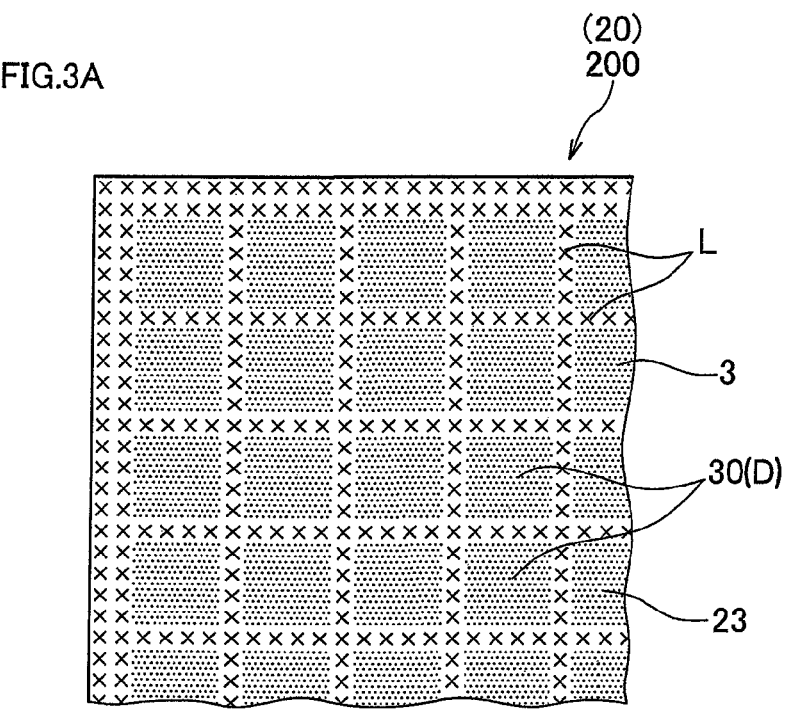
FIG. 3A is a partial enlarged plan view of the absorbent body.

As shown in FIG. 2, the absorbent body 200 includes a top sheet 21 to be in contact with the skin surface of the wearer, a cover sheet 22 to be not in contact with the skin surface, and an absorbent core 23. The top sheet 21 and the cover sheet 22 of FIG. 3B (welded portion) are welded together along lattice-patterned welded lines L and L extending lengthwise and crosswise as shown in FIG. 3A, thereby forming a sandwich structure with the core 23 sandwiched therebetween. That is, as shown in FIG. 3A, the core 23 is surrounded by the top sheet 21 and the cover sheet 22 welded together along the welded lines L and L.

Note that in various figures, welded portions are denoted by "xx".

Figure 3B:
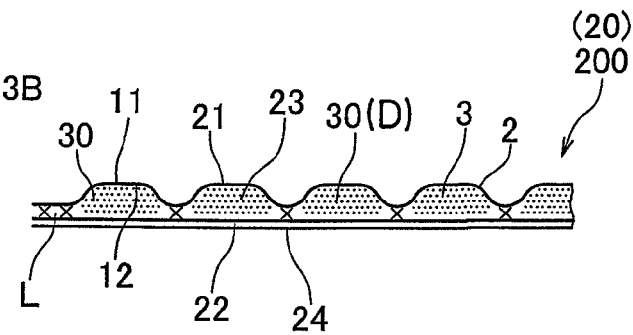
FIG. 3B is a cross-sectional view thereof.

The top sheet 21 and the cover sheet 22 of FIG. 3B are formed by a liquid-permeable and air-permeable non-woven fabric. A liquid-impermeable back sheet 24 is attached to the back surface of the cover sheet 22, with the absorbent body 200 being covered by the back sheet 24.

The core 23 is comprised of a large number of absorbent granular particles 3. Such granular particles 3 are made of an absorbent high molecular polymer well known in the art, wherein the granular particles 3 have an average particle size of about 10 μm to about 1,000 μm prior to absorbing water, and swell after absorbing water to a volume that is several times or hundreds of times larger.

Note that in various figures, the granular particles 3 are denoted by a large number of dots.

The core 23 is formed by aggregate groups 30 each being a collection of a larger number of the granular particles 3, with the aggregate groups 30 being arranged in a large number of arrangement areas D. The aggregate groups 30 and 30 are laid out separately in arrangement areas D and D which are partitioned from one another by lattice-patterned welded lines L and L extending lengthwise and crosswise. That is, arrangement areas D and D in which the aggregate groups 30 and 30 are arranged are partitioned from one another by the welded lines L and L.

In other words, each aggregate group 30 is composed of a collection of a large number of granular particles 3, and one of the aggregate groups 30 and another group thereof are arranged with respect to each other in the lengthwise or crosswise direction with the welded line L, L therebetween, as shown in FIG. 3A. As shown in FIG. 3A, a large number (three of more) of aggregate groups are arranged in the lengthwise and crosswise directions.

Figure 3C:
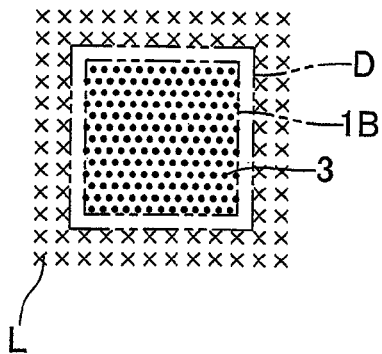
FIG. 3C is an enlarged plan view showing one arrangement area.

FIG. 3C shows one of a plurality of arrangement areas D partitioned from one another in a predetermined pattern, and the vicinity thereof. The one arrangement area D is surrounded by the welded line L.

As shown in the figure, the arrangement area D denoted by a two-dot-chain line is often defined slightly larger than a suction area 1B onto which a plurality of granular particles 3 are drawn by suction.

That is, as shown in the figure, the areas of the arrangement area D and the suction area 1B are often defined so that there is a slight clearance between the welded line L surrounding the arrangement area D and the perimeter of the suction area 1B. That is, the suction area 1B is often contained within the arrangement area D.

In such a case, there is a space provided between the welded line L and the suction area 1B.

Therefore, if some of a plurality of granular particles 3 arranged on the suction area 1B move out of the area of the suction area 1B, the out-of-place granular particles 3 will be placed in the space between the suction area 1B and the welded line L, preventing some of the granular particles from moving out to reach the welded line L.

Note that the arrangement area D and the suction area 1B may be defined as areas of the same size.

Figure 3D:
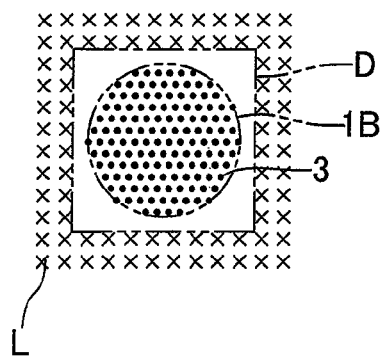
FIG. 3D is an enlarged plan view showing another example of a suction area.

As shown in FIG. 3D, a circular suction area 1B may be contained within a square-shaped arrangement area D.

Each welded line L does not need to be completely continuous, but the welded portions may be formed intermittently to such a degree that it is difficult for granular particles 3 of each aggregate group 30 to move out into other aggregate groups 30.

That is, the welded lines L and L may be formed to such a degree that granular particles 3 in one of the aggregate groups 30 arranged in a predetermined pattern are prevented from moving out into another aggregate group.

The arrangement of the aggregate groups 30 may be of any predetermined pattern, and the aggregate groups 30 do not need to be regularly arranged lengthwise and crosswise. The number of granular particles 3 to be contained within an aggregate group 30 does not need to be generally equal to those of other aggregate groups 30, and there may be a distribution among the aggregate groups 30 in accordance with that of the amount of body fluid to be discharged.

As shown in the enlarged view of FIG. 3A, the aggregate group 30 may be of a rectangular shape or a circular shape having a size of about some mm to about 10 mm. The arrangement pitch between the aggregate groups 30 and 30 may be about 10 mm to about ten-odd mm.

Next, an apparatus for manufacturing the absorbent body 200, i.e., an arrangement apparatus, will be described with reference to FIGS. 4A to 7.

The present arrangement apparatus includes a dispenser device 5, an airflow deflector 6, first, second and third guide rollers 71, 72 and 73 and an ultrasonic horn (an example of an attachment device) 81 around a carrying drum (an example of a carrier device) 4.

The first, second and third guide rollers 71, 72 and 73 are rollers for guiding a carrier web 1, a cover web 2 and a film 9 onto the outer periphery of the drum 4, respectively.

Figure 4A:
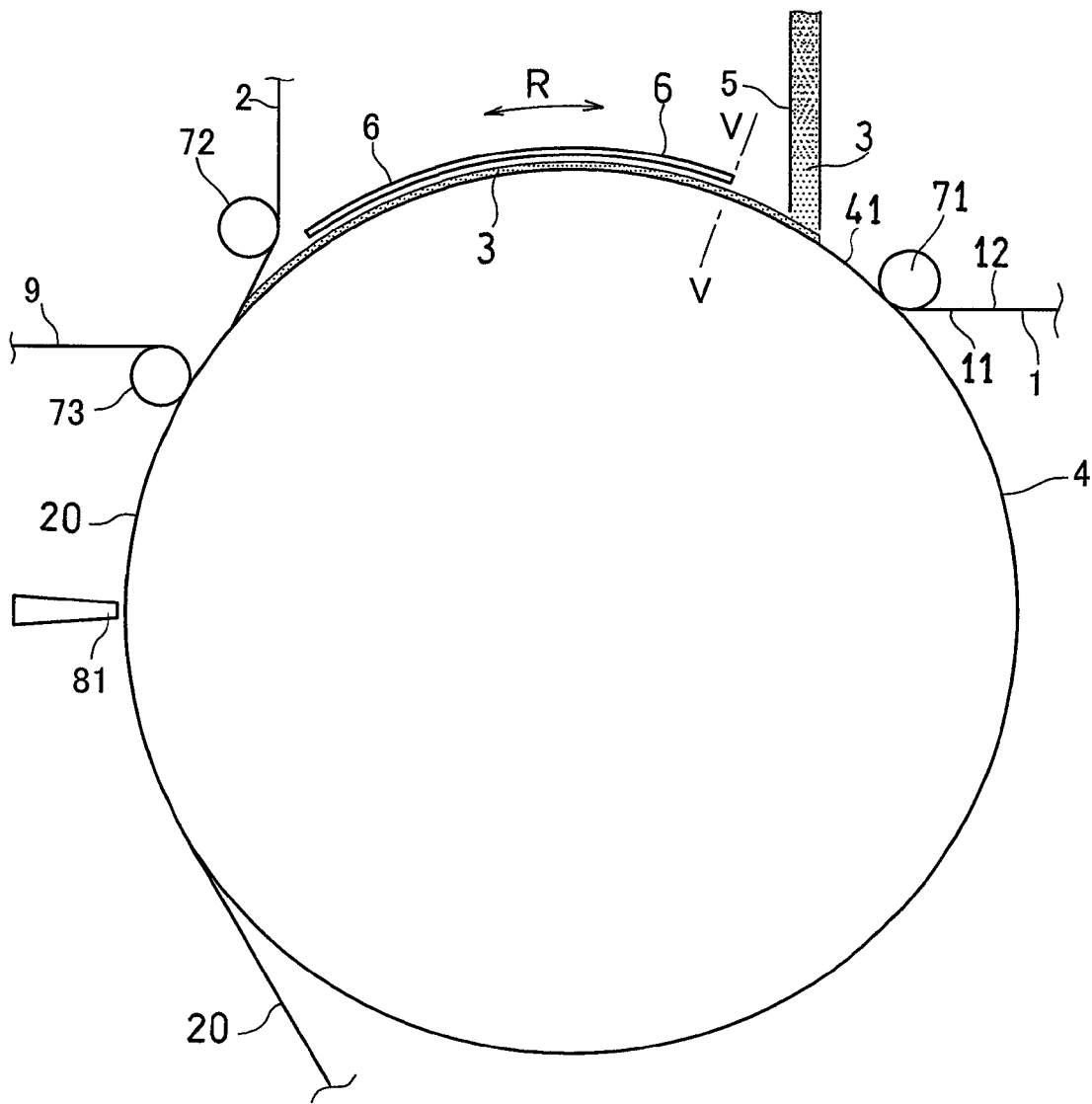
FIG. 4A is a side view showing an apparatus for arranging granular particles, which is an apparatus for manufacturing the absorbent body.
Figure 4B:
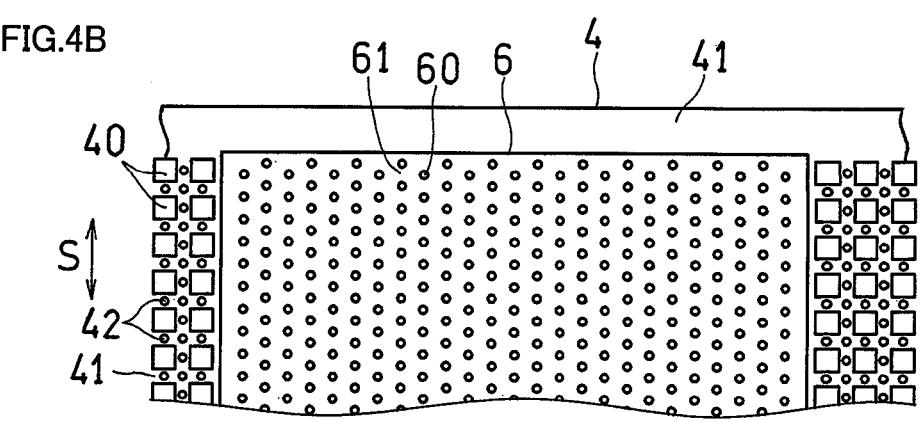
FIG. 4B is a plan view showing an airflow deflector.
Figure 5:
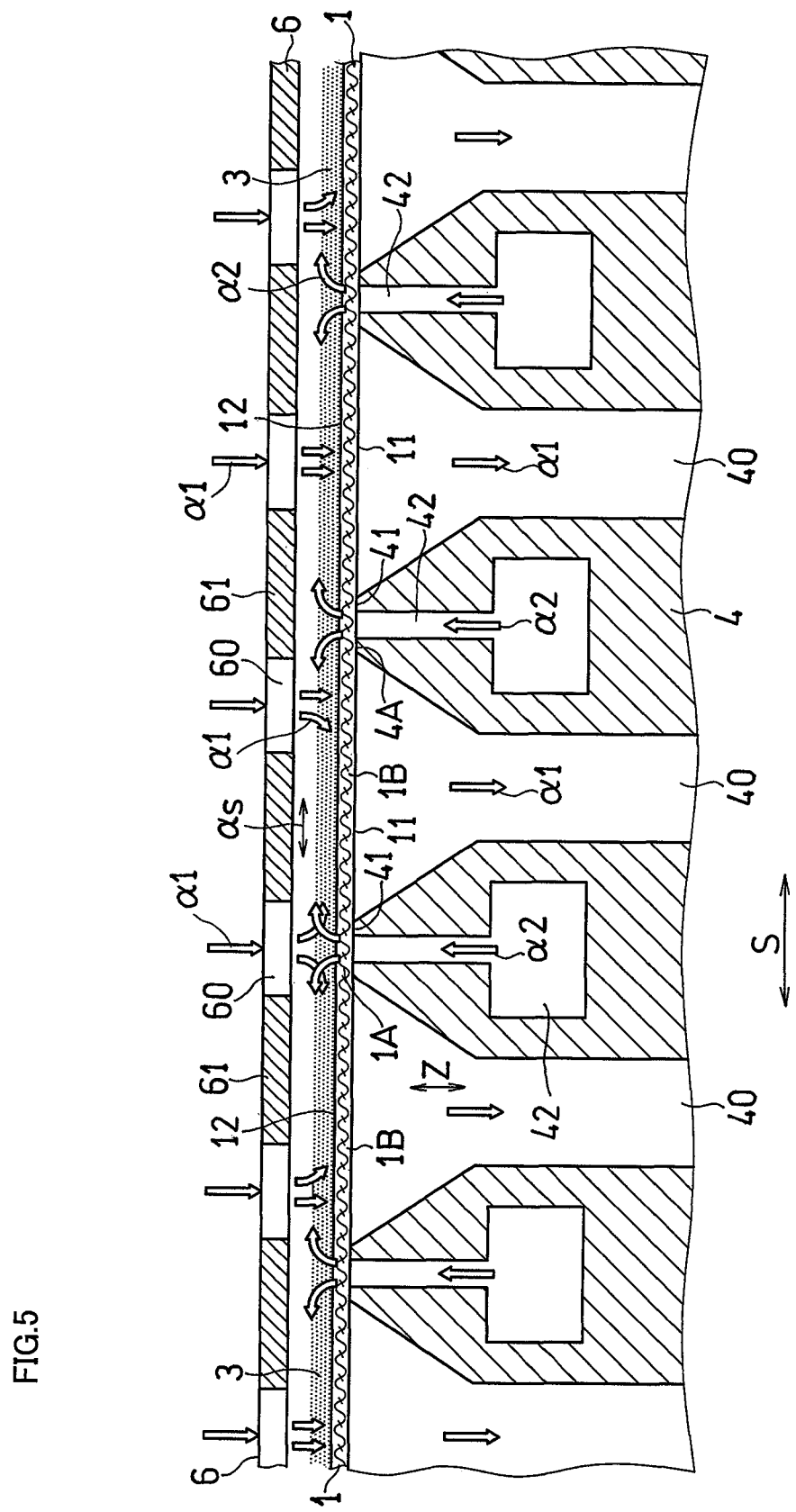
FIG. 5 is an enlarged longitudinal cross-sectional view taken along line V-V of FIG. 4.

As shown in FIG. 5, the drum 4 carries the carrier web 1 along a predetermined carrying path, as shown in FIG. 4, while holding by suction a first surface 11 of the air-permeable carrier web 1 on a carrying surface 41. Note that in FIGS. 5 to 7, the carrier web 1 is drawn to be thicker than it actually is.

The first surface 11 of FIG. 5 forms the skin-contact surface to be in contact with the skin of the wearer.

Figure 6:
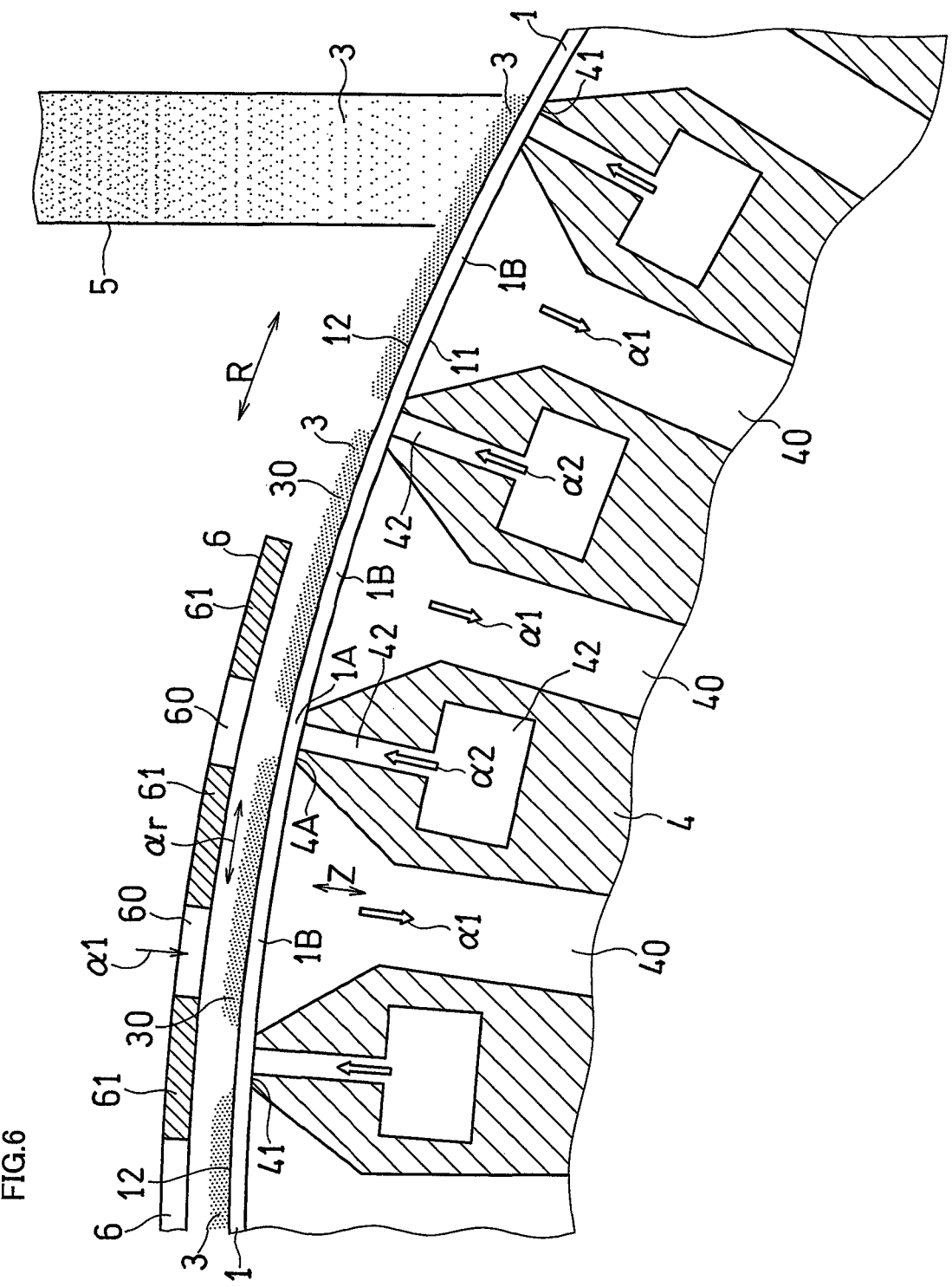
FIG. 6 is an enlarged lateral cross-sectional view of an arrangement apparatus in an area upstream of the airflow deflector.

The dispenser device 5 of FIG. 4 dispenses myriads of granular particles 3 onto a second surface 12 opposite to the first surface 11 of the carrier web 1 being carried of FIG. 6 between the first guide roller 71 and the airflow deflector 6. The myriads of granular particles 3 are dispensed continuously or in intermittent shots of a predetermined amount per unit area of the carrier web 1.

As shown in FIG. 5, a large number of suction holes 40 are provided (open) in the carrying surface 41. Each suction hole 40 communicates with a suction source (negative pressure source) (not shown), and draws a first air α1 into the suction hole 40 through the carrier web 1, thereby holding the granular particles 3 on the second surface 12 of the carrier web 1. The suction holes 40 and the suction source together form a sucker device.

As shown in FIG. 5, discharge holes 42 are provided (open) in the carrying drum 4 in non-suction areas 4A, where the suction is absent, between the suction holes 40 and the suction holes 40. Each discharge hole 42 is open in the non-suction area 4A of the carrying surface 41 for discharging a second air α2.

Each discharge hole 42 communicates with a positive pressure source (not shown) and discharges the second air α2 from the discharge hole 42 toward the second surface 12 of the carrier web 1, so that the granular particles 3 are blown away off a non-suction area 1A of the carrier web 1 by the second air α2 having passed through the carrier web 1 via the second surface 12. The discharge holes 42 and the positive pressure source together form a discharger device.

The airflow deflector 6 is, for example, a punching plate having a large number of through holes 60 therein, and the airflow deflector 6 is curved in conformity to the carrying surface 41 of the carrying drum 4 of FIG. 6 and is arranged close to, and generally parallel to, the carrying surface 41. That is, the airflow deflector 6 is provided opposing the second surface 12 of the carrier web 1 so as to inhibit the flow of the first air α1 in the normal direction Z perpendicular to the second surface 12 of the carrier web 1, thereby giving at least a part of the first air α1 flow components αr and αs (FIG. 5) in the directions R and S (FIG. 5) along the second surface 12 of the carrier web 1.

Note that the airflow deflector 6 is secured to a frame supporting the drum 4, and has a relative velocity in the circumferential direction R with respect to the drum 4 rotating in the circumferential direction R.

The second guide roller 72 of FIG. 4A guides the cover web 2 onto the carrying path of the carrier web 1, downstream of the airflow deflector 6 along the carrying path, so as to produce a sandwich structure 20 (FIG. 7) in which the second surface 12 (FIG. 7) of the carrier web 1 and the granular particles 3 are covered by the cover web 2.

The third guide roller 73 of FIG. 4A guides the film 9 for covering the cover web 2 onto the carrying path of the carrier web 1, downstream of the second guide roller 72 along the carrying path.

The ultrasonic horn 81 gives a vibratory energy to the webs 1 and 2, in cooperation with an anvil (not shown) formed on the carrying surface 41 of the carrying drum 4, downstream of the third guide roller 73 along the carrying path of the carrier web 1. Thus, the carrier web 1 and the cover web 2 are welded together in the non-suction areas 1A of FIG. 7.

With welding (sealing) using ultrasonic vibrations, a mechanical vibration is transferred to the horn 81 of FIG. 4A via an ultrasonic wave, and a thermoplastic web is allowed to pass through between the horn 81 and the anvil while being pressurized, thereby welding the webs together by frictional heat. Therefore, if granular particles 3 remain as a foreign matter in the non-suction area 1A (FIG. 6) between the webs 1 and 2, it will likely lead to a seal failure.

Next, a method for producing the sandwich structure 20 (FIG. 7) will be described.

As shown in FIG. 4A, the carrier web 1 is guided onto the carrying drum 4 by the first guide roller 71, and the carrier web 1 is carried along a predetermined carrying path, i.e., the carrying surface 41 of the carrying drum 4, while holding by suction the first surface 11 (FIG. 6) of the carrier web 1 on the carrying surface 41 of the carrying drum 4.

Between the first guide roller 71 and the airflow deflector 6, the granular particles 3 are dispensed from the dispenser device 5 onto the second surface 12 opposite to the first surface 11 of the carrier web 1 of FIG. 6 being carried. As shown in FIG. 6, the dispensed granular particles 3 form a layer on the second surface 12.

The layer of granular particles 3 may be dispensed in intermittent shots for different absorbent bodies 200 (FIG. 1).

The layer of granular particles 3 may have a greater thickness at the center of the carrying drum 4 in the axial direction thereof than at opposite ends thereof. The layer of granular particles 3 may have a smaller thickness along the perimeter of each absorbent body 200 (FIG. 1) and a greater thickness at or around the center thereof.

Referring to FIG. 5, a plurality of suction holes 40 formed in the carrying surface 41 draw the first air α1 through the carrier web 1, thereby holding the granular particles 3 on the second surface 12 of the carrier web 1. On the other hand, while the first air α1 is being drawn in, the second air α2 is discharged from the discharge holes 42 open in the non-suction area 4A of the carrying surface 41 toward the second surface 12 of the carrier web 1.

With the suction of the first air α1 and the discharge of the second air α2 simultaneously, the granular particles 3 on the non-suction area 1A are blown away by the second air α2 having passed through the carrier web 1 via the second surface 12, and the blown granular particles 3 are drawn in by the first air α1 toward the suction area 1B above the suction hole 40.

As shown in FIG. 6, with the suction and discharge of the air simultaneously, the carrier web 1 holding the granular particles 3 thereon comes close to the airflow deflector 6. Then, the second surface 12 of the carrier web 1 opposes the airflow deflector 6, thereby inhibiting the flow of the first air α1 in the normal direction Z perpendicular to the second surface 12 of the carrier web 1.

That is, a part of the flow of the first air α1 is blocked by a solid portion 61 of the airflow deflector 6 so as to include components αr and αs (FIG. 5) of the flow, and passes through the through holes 60 of the airflow deflector 6 toward the suction holes 40. Therefore, a part of the first air α1 flows along the circumferential direction R of the carrying drum 4 or the axial direction S of FIG. 5 between the airflow deflector 6 and the carrier web 1.

Figure 7:
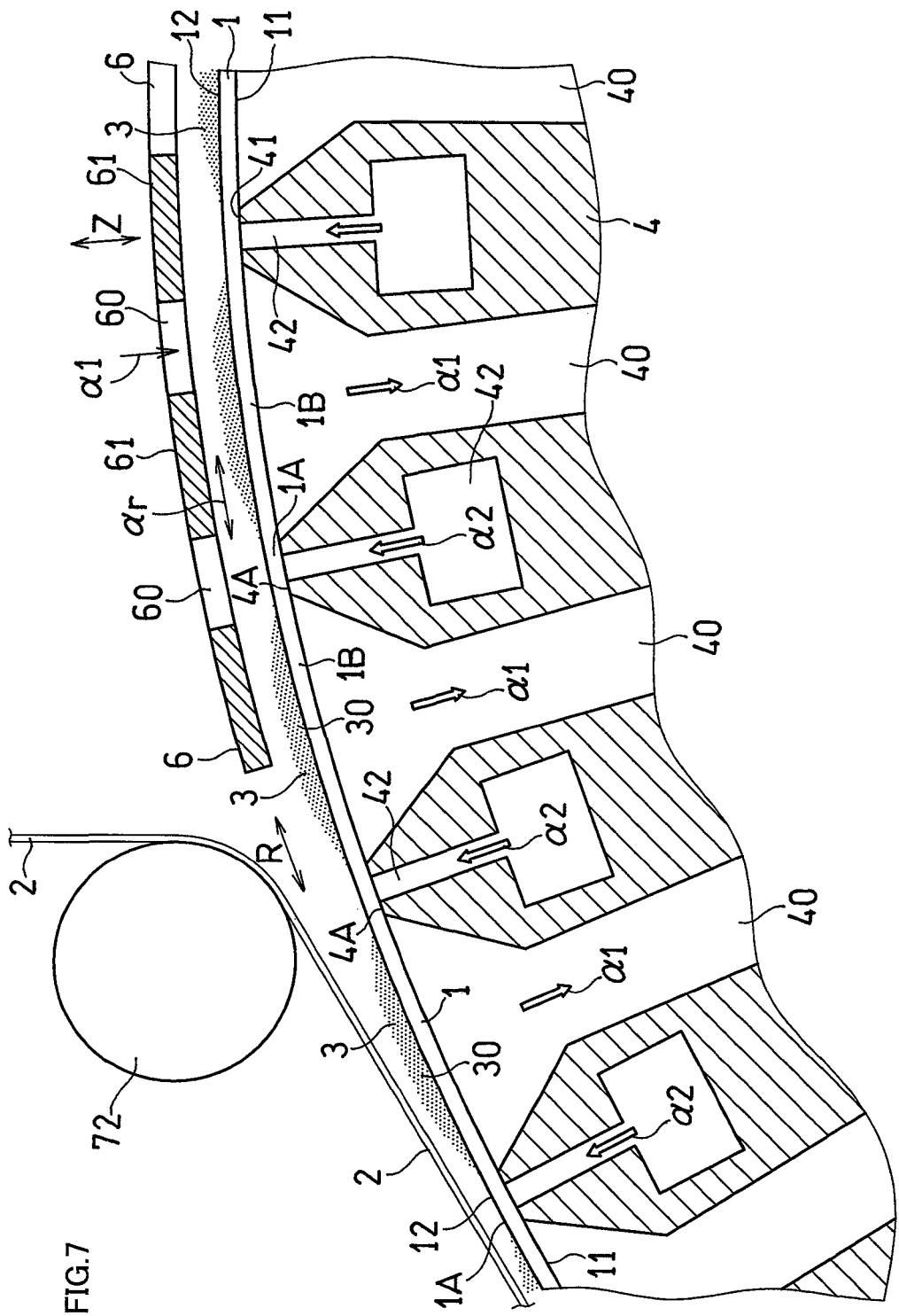
FIG. 7 is an enlarged lateral cross-sectional view thereof in an area downstream of the airflow deflector.

Thus, with the suction of the first air α1 and the discharge of the second air α2 simultaneously, the carrying surface 41 holding the granular particles 3 thereon continues to rotate while opposing the airflow deflector 6, while at least a part of the first air α1 is given flow components αr and αs (FIG. 5) flowing along the second surface 12 of the carrier web 1. Thus, as shown in FIG. 7, granular particles 3 in non-suction areas 1A on the carrier web 1 move into suction areas 1B, whereby the granular particles 3 are arranged in a predetermined pattern on the carrier web 1.

That is, some granular particles 3 in non-suction areas 1A move toward other granular particles 3 being held by suction in suction areas 1B.

As a result, as shown in FIG. 1, aggregate groups 30 each including a plurality of granular particles 3 are arranged on the carrier web 1 so that there is one aggregate group 30 for each of the arrangement areas D partitioned from one another in a predetermined pattern.

After the granular particles 3 are arranged on the carrier web 1 in a predetermined pattern, the carrying surface 41 moves away from the airflow deflector 6, and the second surface 12 of the carrier web 1 and the granular particles 3 are covered by the cover web 2 guided by the second guide roller 72 and the film 9 guided by the third guide roller 73, thus producing the sandwich structure 20.

Then, when the sandwich structure 20 continues to be rotated by the carrying surface 41 to reach the horn 81 of FIG. 4, the carrier web 1 and the cover web 2 are ultrasonically welded together over portions corresponding to the non-suction area 1A of FIG. 2. Thus, the predetermined pattern of the granular particles 3 is maintained. After the webs 1 and 2 are welded together, the suction through the suction holes 40 and the discharge from the discharge holes 42 may be stopped.

Although the cover web 2 of FIG. 3B and the film 9 are also welded together in this welding process, the film 9 may alternatively be bonded via an adhesive to the cover web 2 after the carrier web 1 and the cover web 2 are welded together.

Then, the sandwich structure 20 is cut into unit pieces of individual worn articles, i.e., unit pieces of individual absorbent bodies 200 of FIG. 1.

Embodiment 2

Figure 8:
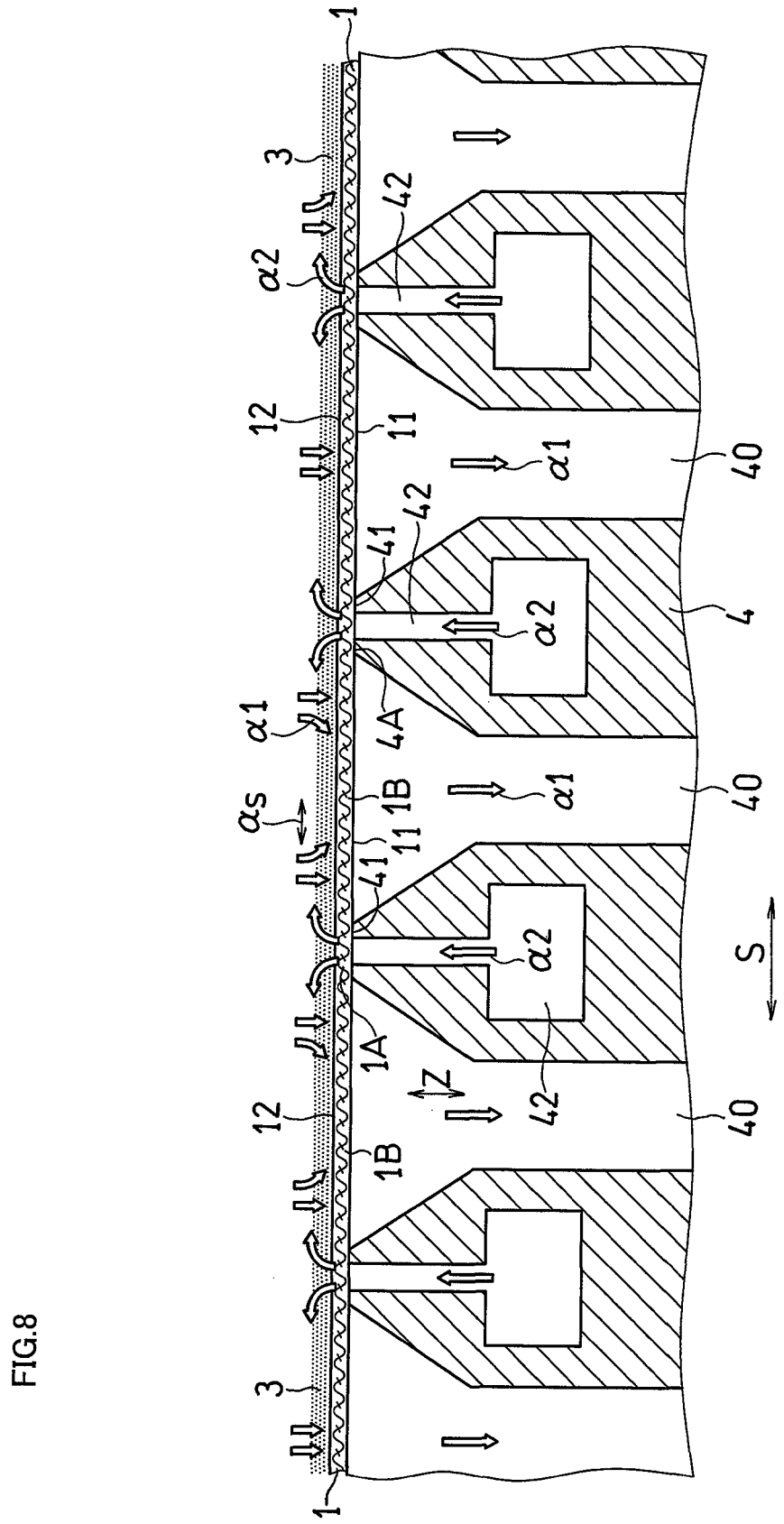
FIG. 8 is an enlarged longitudinal cross-sectional view of an arrangement apparatus, showing another example of an arrangement apparatus.
Figure 9:
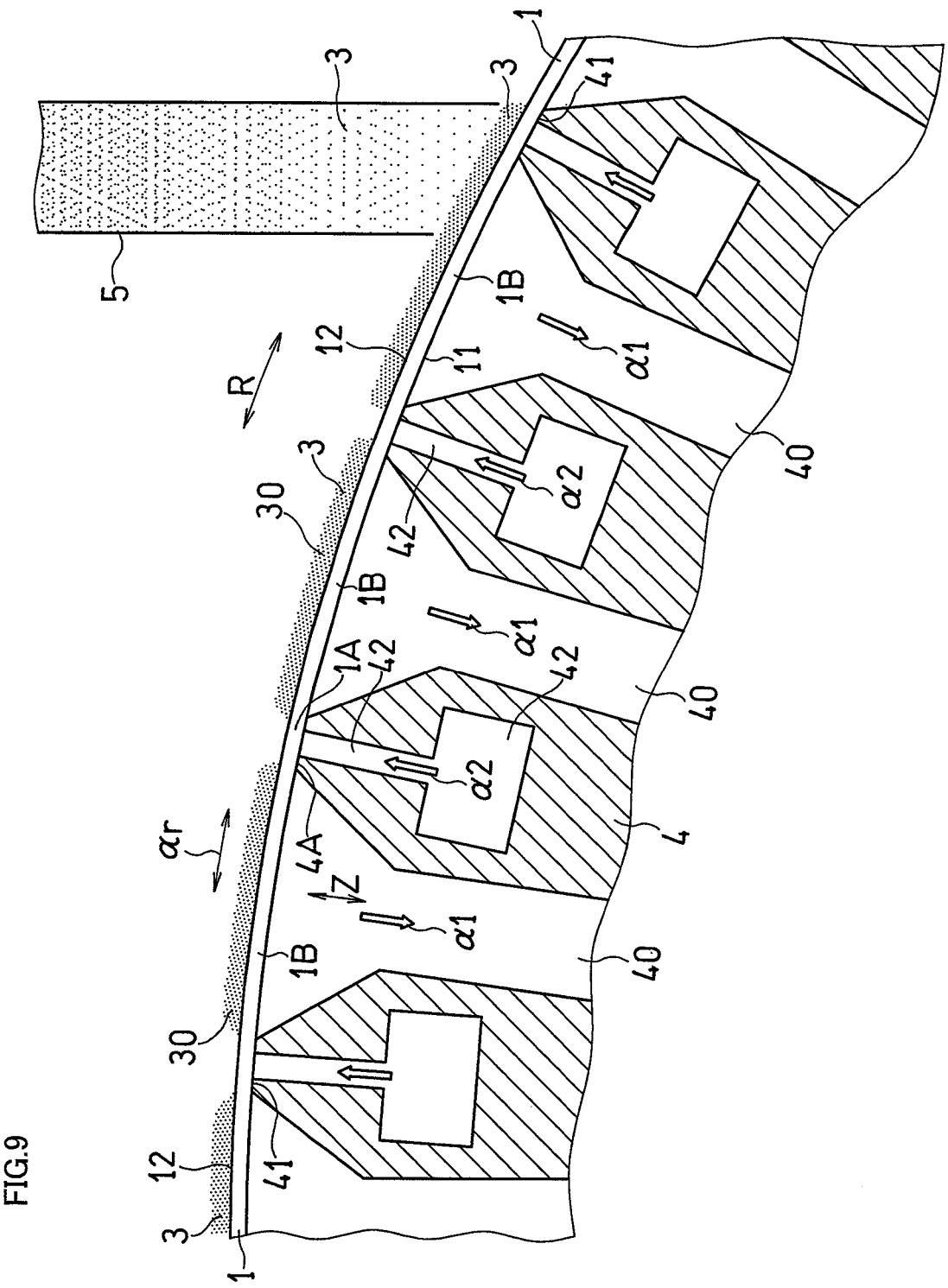
FIG. 9 is an enlarged lateral cross-sectional view of the arrangement apparatus in an upstream area along the carrying path.
Figure 10:
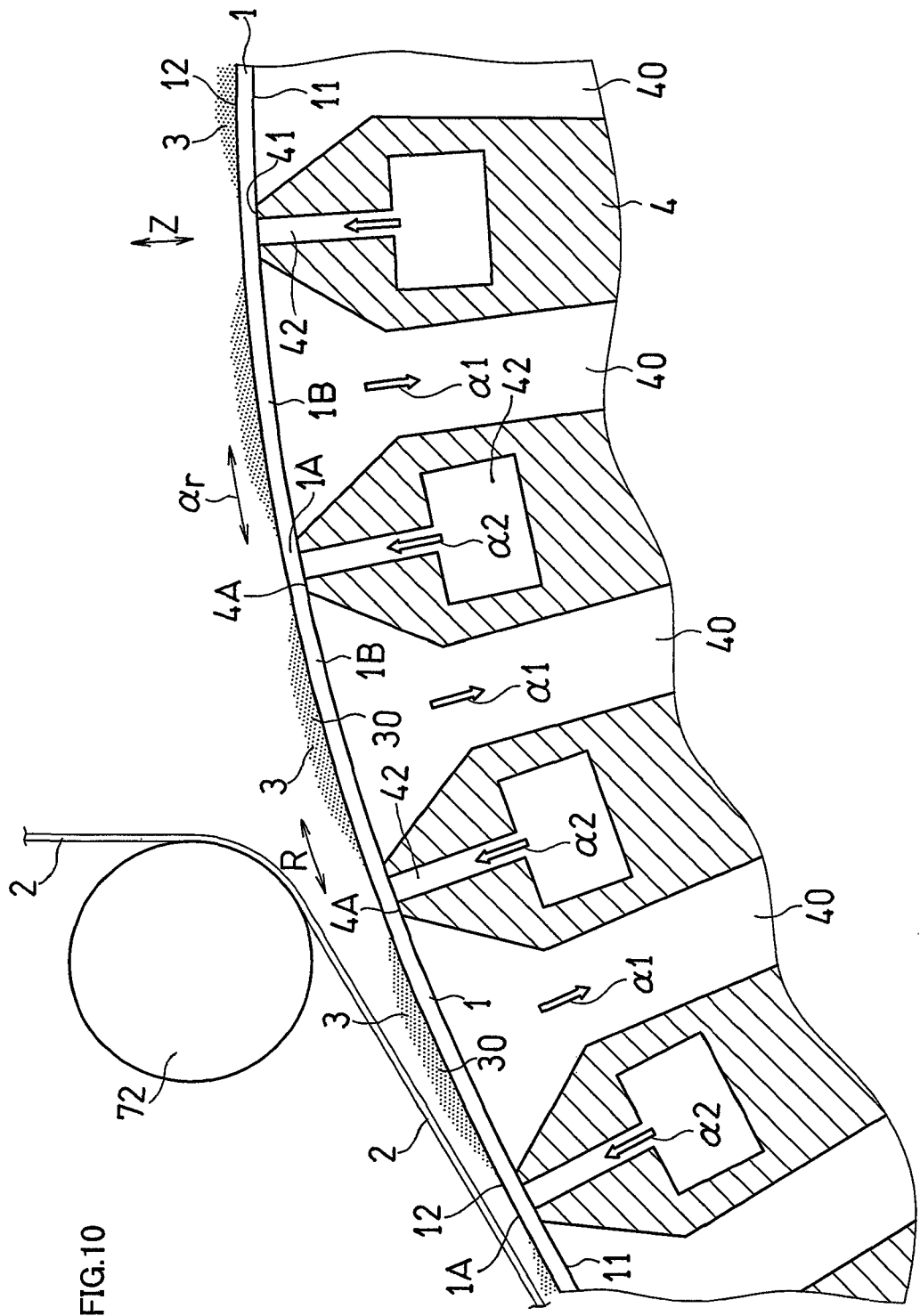
FIG. 10 is an enlarged lateral cross-sectional view thereof in a downstream area along the carrying path.

FIGS. 8 to 10 show Embodiment 2.

As shown in these figures, the airflow deflector is not provided in the present embodiment. Also in this embodiment, as in the above example of FIGS. 5 to 7, granular particles 3 in non-suction areas 1A of the carrier web 1 are likely to gather in suction areas 1B as the carrier web 1 moves downstream along the carrying path, as shown in FIGS. 8 to 10.

In Embodiment 2, the method by which the granular particles 3 are arranged on the suction areas 1B of the carrier web 1 is substantially the same as that of Embodiment 1, and will not be described below.

In Embodiment 2, as opposed to Embodiment 1, it is not possible to realize the action of giving the flow of the first air α1 flow components in the circumferential direction αr or the axial direction as by means of an airflow deflector. Therefore, the action of collecting the granular particles 3 blown away by the discharge of the second air α2 in the suction area 1B will be lower than that of Embodiment 1.

Note that in Embodiment 2, the density with which the discharge holes 42 are provided may be increased with respect to that of Embodiment 1.

Otherwise, the configuration is substantially the same as that of Embodiment 1, and like elements will be denoted by like reference numerals and will not be further described below.

Figure 11A:
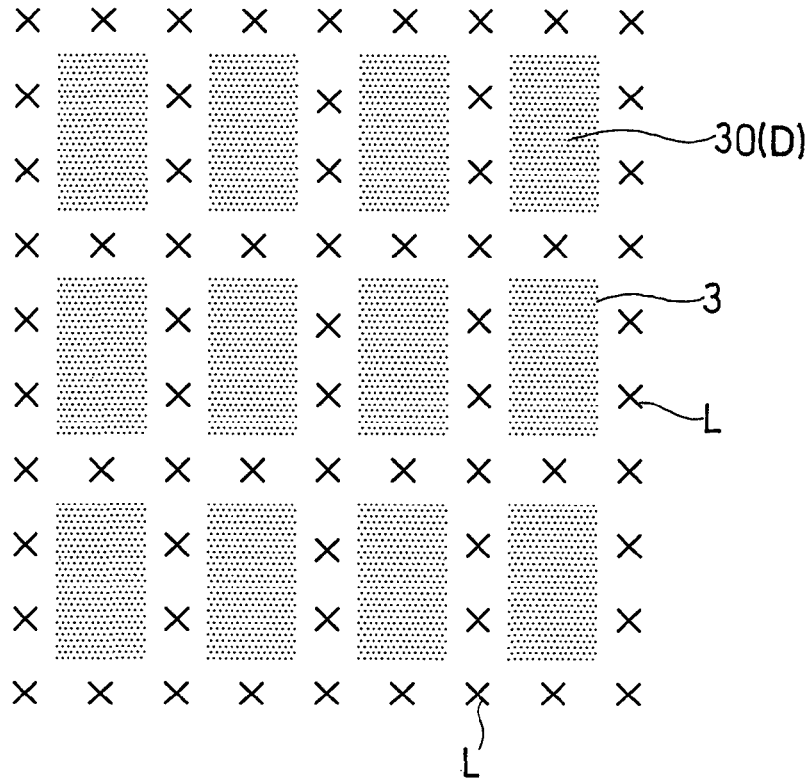
FIGS. 11A and 11B are plan views each showing another example of an arrangement pattern and a seal pattern.
Figure 11B:
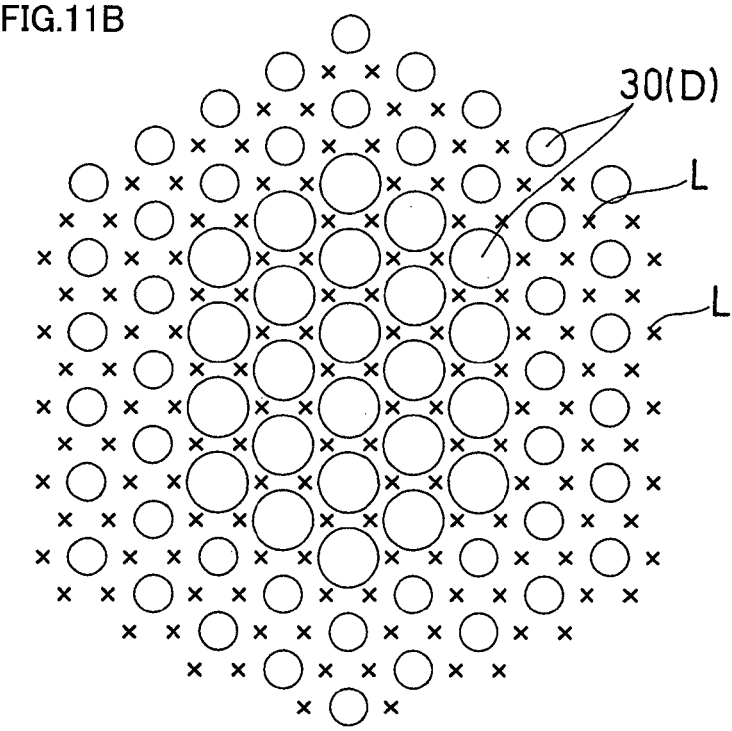

FIGS. 11A and 11B show another example of an arrangement pattern and a seal pattern of the granular particles 3.

The shape of the aggregate group 30 (arrangement area D) of the granular particles 3 in the arrangement pattern may be rectangular as shown in FIG. 11A or circular as shown in FIG. 11B. The layout of the aggregate group 30 of the granular particles 3 may be a lengthwise-crosswise layout as shown in FIG. 11A or a triangular layout as shown in FIG. 11B.

The seal pattern for partitioning the aggregate groups 30 (arrangement areas D) of the granular particles 3 from one another may be continuous lines as shown in FIG. 1 or an intermittent dotted pattern as shown in FIGS. 11A and 11B.

While preferred embodiments have been described above with reference to the drawings, obvious variations and modifications will readily occur to those skilled in the art upon reading the present specification.

For example, the carrier device may be a conveyer, instead of a drum.

The method of attachment between the carrier web 1 and the cover web 2 may be an attachment method using thermal welding such as heat seal, for example, instead of ultrasonic welding.

As used in the present invention, "a plurality of granular particles" is a concept including cases where a powdery material is mixed with a plurality of granular particles, as well as cases where they are made only of an aggregate or aggregates of a granular material.

Thus, such changes and modifications are deemed to fall within the scope of the present invention, which is defined by the appended claims.

INDUSTRIAL APPLICABILITY

The present invention is applicable to cases where granular particles are arranged in a predetermined pattern in addition to an absorbent body of a disposable worn article.

REFERENCE SIGNS LIST

1: Carrier web, 1A: Non-suction area, 1B: Suction area, 11: First surface, 12: Second surface
2: Cover web, 20: Sandwich structure, 21: Top sheet, 22: Cover sheet, 23: Core, 24: Back sheet
3: Granular particles, 30: Aggregate group, D: Arrangement area
4: Carrying drum, 4A: Non-suction area, 40: Suction holes, 41: Carrying surface, 42: Discharge hole
5: Dispenser device
6: Airflow deflector, 60: Through holes, 61: Solid portion, 62: Plate
71: First guide roller, 72: Second guide roller, 73: Third guide roller
81: Ultrasonic horn
9: Film
100: Worn article, 200: Absorbent body (diaper body), 201: Front portion, 202: Back portion, 203: Crotch portion, 301: Front girth portion, 302: Back girth portion
α1: First air, α2: Second air, αr and αs: Flow components
R: Circumferential direction, S: Axial direction, Z: Normal direction

The invention claimed is:

1. A method for arranging a plurality of granular particles in each of a plurality of arrangement areas which are partitioned from one another in a predetermined pattern, the method comprising the steps of:
   carrying an air-permeable carrier web along a predetermined carrying path while holding a first surface of the carrier web on a carrying surface of a carrier device;
   dispensing the granular particles onto a second surface, opposite to the first surface, of the carrier web being carried;
   drawing a first air from a plurality of suction holes repeatedly alternating, in a first direction, with discharge holes formed in the carrying surface along the first direction and from a plurality of suction holes repeatedly alternating, in a second direction intersecting with the first direction, with discharge holes formed in the carrying surface along the second direction through the carrier web, thereby holding some of the plurality of granular particles on each suction area on the second surface of the carrier web corresponding to one of the suction holes; and
   while drawing the first air, discharging a second air from the discharge holes open in non-suction areas that repeatedly alternate with the suction holes in the first direction and the second direction toward the second surface of the carrier web, whereby some other ones of the plurality of granular particles on the non-suction areas blown away by the second air having passed through the carrier web via the second surface toward at least one of the suction areas, thus arranging the granular particles in each of the arrangement areas in the predetermined pattern on the carrier web.

2. A method according to claim 1, further comprising the steps of:
   after the step of arranging the granular particles in the predetermined pattern, covering the second surface of the carrier web and the granular particles by a cover web, thereby producing a sandwich structure; and
   attaching the carrier web and the cover web together over a portion corresponding to the non-suction area in order to prevent the granular particles in the arrangement areas arranged in the predetermined pattern from moving from one of the plurality of arrangement areas to another.

3. A method according to claim 2, wherein the attachment step is performed by welding the webs together.

4. A method according to claim 3, further comprising the step of giving at least a part of the first air a flow component flowing in a direction along the second surface of the carrier web by means of an airflow deflector opposing the second surface of the carrier web, thereby moving the some other ones of the plurality of granular particles on the non-suction area on the carrier web toward at least one of the suction areas, thus arranging the granular particles in the predetermined pattern on the carrier web.

5. An apparatus for arranging a plurality of granular particles in each of a plurality of arrangement areas which are partitioned from one another in a predetermined pattern, the apparatus comprising:
a carrier device for carrying an air-permeable carrier web along a predetermined carrying path while holding a first surface of the carrier web on a carrying surface thereof;
a dispenser device for dispensing the granular particles onto a second surface, opposite to the first surface, of the carrier web being carried;
a sucker device comprising a plurality of suction holes repeatedly alternating, in a first direction, with discharge holes formed in the carrying surface along the first direction and from a plurality of suction holes repeatedly alternating, in a second direction intersecting with the first direction, with discharge holes formed in the carrying surface along the second direction for drawing a first air into the suction holes through the carrier web, thereby sucking some of the plurality of granular particles onto each suction area on the second surface of the carrier web corresponding to one of the suction holes; and a discharger device comprising the discharge holes open in non-suction areas that repeatedly alternate with the suction holes in the first direction and the second direction for discharging a second air from the discharge holes toward the second surface of the carrier web, while the first air is being drawn, whereby some other ones of the plurality of granular particles on the non-suction areas are blown away by the second air having passed through the carrier web via the second surface.

6. An arrangement apparatus according to claim 5, further comprising:
a guide device for guiding the cover web onto the carrying path, while the suction and the discharge are being performed, in order to produce a sandwich structure in which the second surface of the carrier web and the granular particles are covered by a cover web; and
an attachment device for attaching the carrier web and the cover web together over a portion corresponding to the non-suction area in order to prevent the granular particles in the arrangement areas arranged in the predetermined pattern from moving from one of the plurality of arrangement areas to another.

7. An arrangement apparatus according to claim 6, wherein the attachment device is a welder device for welding the webs together.

8. An arrangement apparatus according to claim 7, further comprising an airflow deflector opposing the second surface of the carrier web, upstream of the guide device along the carrying path of the carrier web, for giving at least a part of the first air a flow component flowing in a direction along the second surface of the carrier web.

9. An arrangement apparatus according to claim 5, wherein the first direction is set to a carrying direction of the carrier web, and the second direction is set to a direction intersecting with the carrying direction.

* * * * *